United States Patent
Labyed et al.

(10) Patent No.: US 10,646,202 B2
(45) Date of Patent: May 12, 2020

(54) SHEER SPEED IMAGING USING COHERENCE

(71) Applicant: Siemens Medical Solutions USA, Inc., Malvern, PA (US)

(72) Inventors: Yassin Labyed, Maple Valley, WA (US); Liexiang Fan, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 539 days.

(21) Appl. No.: 15/413,203

(22) Filed: Jan. 23, 2017

(65) Prior Publication Data

US 2018/0206823 A1    Jul. 26, 2018

(51) Int. Cl.
*A61B 8/00* (2006.01)
*A61B 8/08* (2006.01)

(52) U.S. Cl.
CPC ............ *A61B 8/485* (2013.01); *A61B 8/5207* (2013.01); *A61B 8/5223* (2013.01); *A61B 8/5238* (2013.01); *A61B 8/463* (2013.01); *A61B 8/466* (2013.01); *A61B 8/469* (2013.01); *A61B 8/483* (2013.01)

(58) Field of Classification Search
CPC ..... A61B 8/5238; A61B 8/484; A61B 8/5223; A61B 8/5207; A61B 8/483; A61B 8/466; A61B 8/469; A61B 8/463
See application file for complete search history.

(56) References Cited

U.S. PATENT DOCUMENTS

| | | | |
|---|---|---|---|
| 8,267,865 B2 | 9/2012 | Hoyt et al. | |
| 9,125,547 B2 | 9/2015 | Xie et al. | |
| 2008/0249408 A1* | 10/2008 | Palmeri | A61B 8/08 600/438 |
| 2012/0089019 A1 | 4/2012 | Fan | |
| 2013/0218011 A1* | 8/2013 | Benson | A61B 8/485 600/438 |
| 2014/0180091 A1 | 6/2014 | McAleavey | |
| 2015/0094579 A1 | 4/2015 | Fan | |
| 2016/0192906 A1 | 7/2016 | Lee et al. | |

FOREIGN PATENT DOCUMENTS

| | | |
|---|---|---|
| KR | 2015-0037689 A | 4/2015 |
| KR | 1586998 B1 | 1/2016 |
| KR | 2016-0041925 A | 4/2016 |

OTHER PUBLICATIONS

Chen, Shigao, et al. "Quantification of liver stiffness and viscosity with SDUV: In vivo animal study." 2008 IEEE Ultrasonics Symposium. IEEE, 2008.

(Continued)

*Primary Examiner* — Mallika D Fairchild

(57) ABSTRACT

To increase the signal-to-noise ratio for displacements used to estimate the shear speed in patient tissue, constructive interference from multiple shear waves is used. By transmitting acoustic radiation force impulses focused at different locations, the resulting shear waves may constructively interfere within a region of interest. This constructive interference causes a greater amplitude of displacement. The location of this more easily detected greater interference and the difference in time of the transmitted acoustic radiation force impulses are used to estimate the shear wave speed for the tissue.

11 Claims, 5 Drawing Sheets

(56) References Cited

OTHER PUBLICATIONS

McLaughlin, Joyce, et al. "Shear wave speed recovery using moving interference patterns obtained in sonoelastography experiments." The Journal of the Acoustical Society of America 121.4 (2007): 2438-2446.
Nabavizadeh, Alireza, et al. "Multi-source and multi-directional shear wave generation with intersecting steered ultrasound push beams." IEEE transactions on ultrasonics, ferroelectrics, and frequency control 62.4 (2015): 647-662.
Rosenzweig, Stephen, Mark Palmeri, and Kathryn Nightingale. "Analysis of rapid multi-focal-zone ARFI imaging." IEEE transactions on ultrasonics, ferroelectrics, and frequency control 62.2 (2015): 280-289.
Scola, Mallory R., Leslie M. Baggesen, and Caterina M. Gallippi. "Multi-Push (MP) acoustic radiation force (ARF) ultrasound for assessing tissue viscoelasticity, in vivo." 2012 Annual International Conference of the IEEE Engineering in Medicine and Biology Society. IEEE, 2012.
Song, Pengfei, et al. "Two-dimensional shear-wave elastography on conventional ultrasound scanners with time-aligned sequential tracking (TAST) and comb-push ultrasound shear elastography (CUSE)." IEEE transactions on ultrasonics, ferroelectrics, and frequency control 62 (2015): 290-302.
Wu, Zhe, et al. "Sonoelastographic imaging of interference patterns for estimation of the shear velocity of homogeneous biomaterials." Physics in medicine and biology 49.6 (2004): 911.

* cited by examiner

SHEER SPEED IMAGING USING COHERENCE

BACKGROUND

The present embodiments relate to shear speed imaging. The shear speed of tissue may be diagnostically useful, so ultrasound is used to estimate the shear speed of a patient's tissue. By transmitting an acoustic radiation force impulse (ARFI), a shear wave is generated at the ARFI focus. Ultrasound scanning monitors the propagation of the shear wave. The time-to-peak displacement at a distance from the origin of the shear wave is used to determine the velocity of the shear wave in the tissue.

Penetration is a problem in shear wave speed imaging. The attenuation of the acoustic push pulse (i.e., ARFI) and the safety limits for ultrasound power result in weaker push pulses at deeper depths. The signal-to-noise ratio may result in failure to obtain an accurate velocity estimate. The estimated shear speed values become unreliable. Even at shallower depths, the signal-to-noise ratio may result in less reliability in the estimate, especially for stiffer tissue (e.g., fibrotic liver).

SUMMARY

By way of introduction, the preferred embodiments described below include methods, computer readable storage media with instructions, and systems for shear speed imaging. To increase the signal-to-noise ratio for displacements used to estimate the shear speed, constructive interference from multiple shear waves is used. By transmitting ARFI focused at different locations, the resulting shear waves may constructively interfere within a region of interest. This constructive interference causes a greater amplitude of displacement. The location of this more easily detected greater interference and the difference in time of the transmitted ARFIs are used to estimate the shear wave speed for the tissue.

In a first aspect, a method is provided for shear speed imaging with an ultrasound scanner. First and second acoustic radiation force pulses are transmitted from a transducer of the ultrasound scanner to opposite sides of a region of interest of tissue of a patient and separated in time by a first amount. First and second shear waves are generated on the opposite sides due to the first and second acoustic radiation force pulses. The ultrasound scanner repetitively scans the region of interest with ultrasound as the first and second shear waves propagate in the region of interest. A location of a greater displacement in the region of interest due to coherence of the first and second shear waves at the location is detected. The location is determined from data obtained by the scanning. A shear wave speed of the tissue is calculated as a function of the first amount of the time and the location. An image of the shear wave speed of the tissue of the patient is generated.

In a second aspect, a method is provided for shear speed imaging with an ultrasound scanner. Displacements are detected as a function of locations for different times. The displacements are responsive to a plurality of shear waves generated by a plurality of pushing pulses transmitted to different foci. A position for constructive interference of the shear waves is determined based on the displacements. A shear wave speed is calculated based on the position of constructive interference relative to the different foci and a time difference between the pushing pulses. An output of the shear wave speed is generated.

In a third aspect, a system is provided for shear speed imaging. A transmit beamformer is configured to transmit first and second pulses at different times to different locations relative to tissue of a patient. A receive beamformer is configured to receive signals from scanning after the different times. A processor is configured to determine, from the signals, a velocity of shear in the tissue based on a difference in location of a greatest amplitude from shear waves responsive to the first and second pulses from a half-way point between the different locations and a difference of the different times. A display is configured to output the velocity.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Shear speed imaging uses coherence of shear waves to increase signal-to-noise ratio (SNR). To estimate shear wave speed, constructive interference of shear waves from multiple ARFI push pulses is used. For example, the shear wave speed is estimated using the constructive interference of the waves resulting from two push pulses at different sides of the region of interest (ROI). The large tissue displacements at the location of constructive interference result in high SNR, which improves the success rate of the shear wave speed measurements, especially at deep depths.

In one embodiment, two ARFI push pulses, one at each side of the ROI, are transmitted. The two push pulses are separated in time by $\Delta t$ and are at a same distance from a center of the ROI. The shear waves from the two ARFI push pulses create an interference pattern. At one location at distance $\Delta x$ from the center of the ROI, the two waves interfere constructively (i.e., coherently sum), resulting in a high displacement magnitude. The location is detected using ultrasound scanning. The shear wave speed is estimated from $\Delta x$ and $\Delta t$. The process may be repeated for different regions to show distribution of shear wave speed in the tissue of interest.

Figure 1:
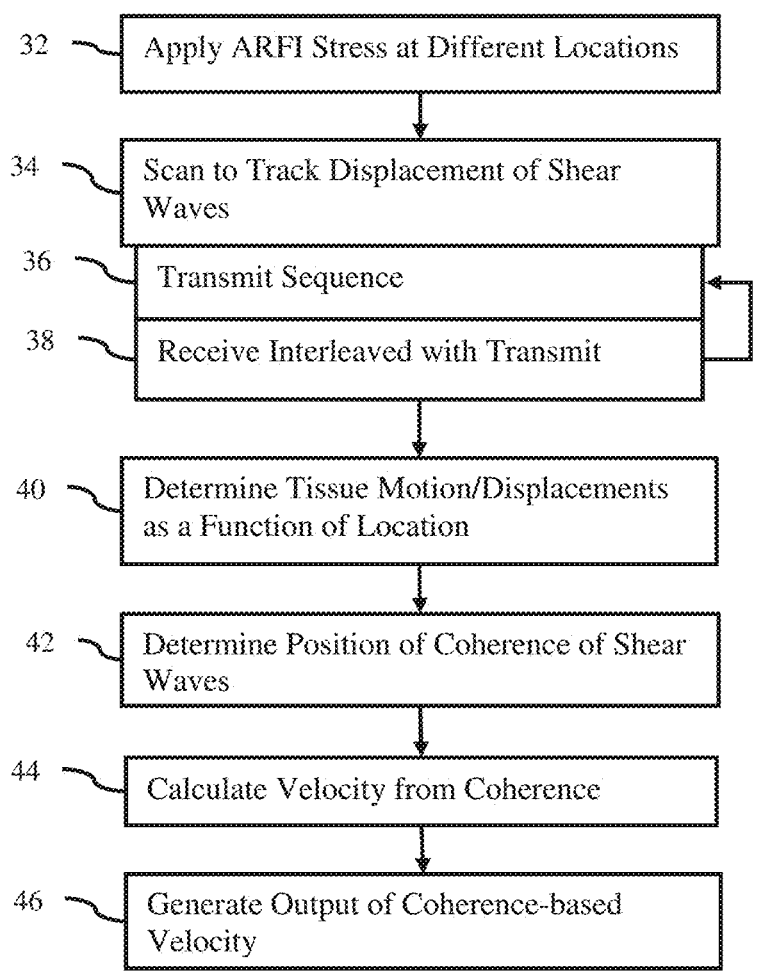
FIG. 1 is a flow chart diagram of one embodiment of a method for shear speed imaging with an ultrasound scanner.

FIG. 1 shows one embodiment of a method for shear speed imaging with an ultrasound scanner. Multiple shear waves are generated and constructively interfere. The constructive interference causes a greater displacement, resulting in greater SNR than if just one shear wave were used. The location of constructive interference is detected with ultrasound scanning. This location may be used to estimate the shear wave speed in the tissue. For estimating shear speed at greater depths (e.g., greater than 5, 6, or 8 cm), the shear speed estimate is more reliable due to the use of constructive interference. For example, ARFIs are transmitted with foci at a depth greater than 8 cm. The location of constructive interference is detected at the depth greater than 8 cm. The shear wave speed at the depth greater than 8 cm is estimated.

Figure 5:
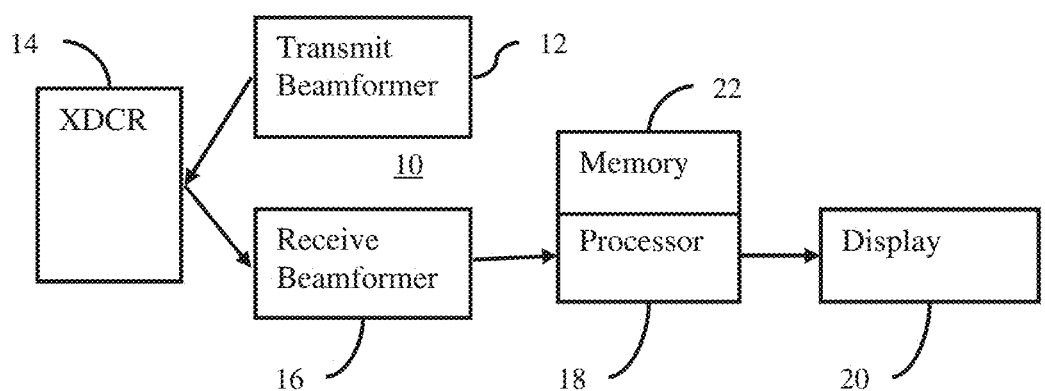
FIG. 5 is a block diagram of one embodiment of a system for shear speed imaging.

The method is implemented by the system of FIG. 5 or a different system. Transmit and receive beamformers use a transducer to transmit and receive from the patient, including applying ARFI and tracking the tissue response in acts 32-38. A processor determines the tissue motion, determines the location of constructive interference, calculates the velocity, and generates the image in acts 40-46. A display may be used for act 46. Different devices, such as other parts of an ultrasound scanner, may perform any of the acts.

The acts are performed in the order described or shown (i.e., top to bottom), but may be performed in other orders. For example, act 34 may be at least partly interleaved between the transmission of the ARFIs in act 32. As another example, as acts 36 and 38 are repeated, act 40 may be interleaved or simultaneously performed (e.g., calculating displacements as the scanning provides information and is repeated).

Additional, different, or fewer acts may be provided. For example, acts for configuring the ultrasound scanner, positioning the transducer, and/or recording results are provided. In another example, reference scanning is performed prior to act 32. In alternative embodiments, the initial scan of acts 36 and 38 after generation of the shear waves is used as the reference scan.

To determine tissue motion caused by shear waves, the tissue in a relaxed state or subject to no or relatively little shear wave is detected as a reference. The ultrasound scanner detects reference tissue information. The scanning occurs prior to transmission of the ARFI in act 32, but may be performed at other times.

To scan for the reference information, a sequence of imaging pulses is transmitted to tissue prior to application of a stress. Since the tissue response to the stress may be measured before, after or both relative to the peak stress, the transmission for reference tissue position is performed prior to application of the stress or after the tissue returns to a relaxed state.

The sequence is the same as provided in act 36, such as being a sequence of pulses all having a same frequency band and center frequency. One set of N pulses is transmitted before ARFI is applied and is used to acquire reference data for displacement estimation. N may be any positive integer for each spatial location or group of spatial locations. Any type of detection may be used, such as a B-mode detection of the intensity. In other embodiments, the beamformed data without detection is used as the reference.

In act 32, the ultrasound scanner uses the transducer to apply stress to the tissue. For example, ARFI focused at a point is transmitted. When ARFI is applied to a focused area, the tissue responds to the applied force by moving. The ARFI creates a shear wave that propagates laterally through the tissue. The shear wave causes displacement of the tissue. At each given spatial location spaced from the focus, this displacement increases and then recovers to zero, resulting in a temporal displacement profile. The tissue properties affect the displacement.

The ARFI may be generated by a cyclical pulsed waveform of any number of cycles (e.g., tens or hundreds of cycles). For example, ARFI is transmitted as a pushing pulse with 100-1000 cycles. The transmitted acoustic wave propagates to the region of interest, causing a deposition of energy and inducing a shear wave.

For coherent interference, two or more shear waves are generated. For example, two ARFIs are transmitted from a transducer of the ultrasound scanner. The different ARFIs have some of the same characteristics, such as being at a same center frequency with a same frequency band generated with a same number of cycles, transmit aperture, amplitude, and apodization profile. These characteristics may be different for different ARFIs. Other characteristics may be the same or different.

The ARFIs are transmitted as pushing pulses with different foci. The foci for generating the shear waves are at different locations so that different shear waves are generated, allowing for coherent summation at a different location than either of the foci. In one embodiment, the foci are all at a same depth, but different lateral locations. For tracking displacements, a ROI is used. This ROI is set by the user and/or is set based on the spatial distribution of simultaneous receive beams used for tracking. The foci are at different positions relative to the ROI. The foci are in and/or outside of the ROI. For example, the different foci are outside the ROI on opposite sides of the ROI. In one embodiment, the ROI is 5 mm wide, with the foci on opposite sides 4.5 mm from the center of the ROI. The foci are equal distance from the center, but may be at unequal distances from the center of the ROI. The foci and the center of the ROI are at a same depth, but may be at different depths. Any spatial distribution of the foci may be used.

Figure 2:
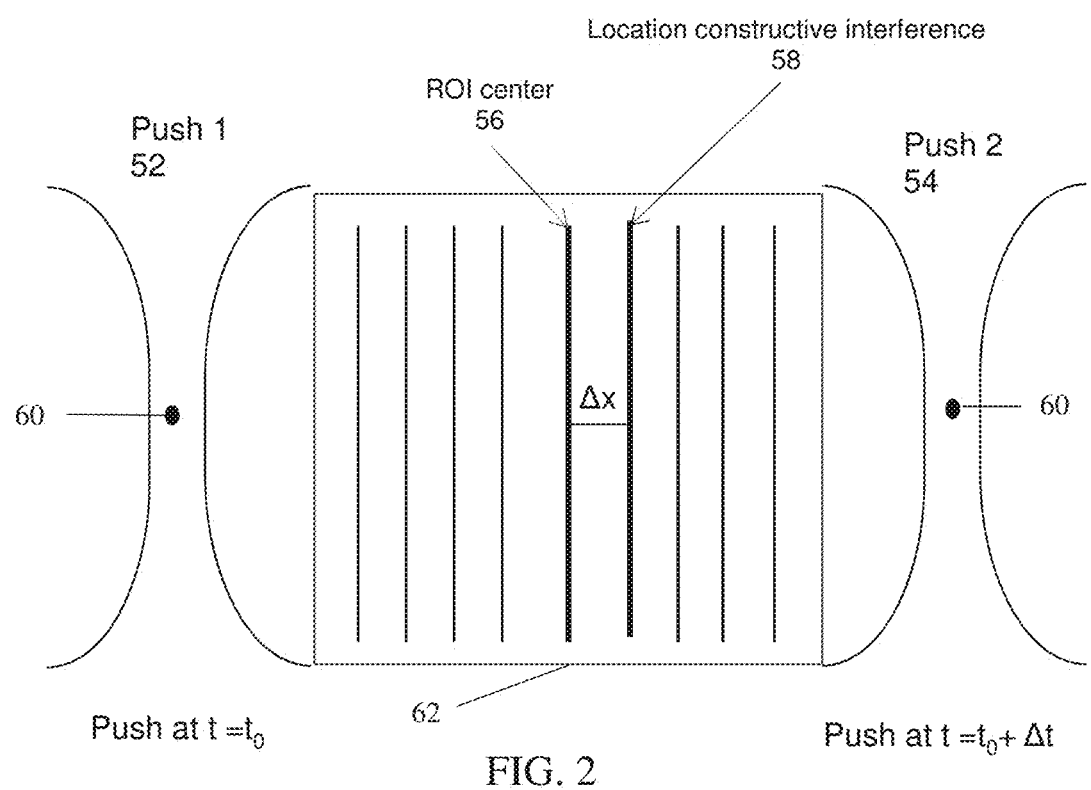
FIG. 2 illustrates an example spatial and temporal transmit distribution for detection of constructive interference from multiple shear waves.

FIG. 2 shows an example. Two pushing pulses 52, 54 (i.e., ARFI transmit beams) are generated with foci 60 on opposite sides of a ROI 62. The ROI 62 includes a plurality of scan lines (odd number in this example) used for tracking, including a scan line at the center 56. An even number of scan lines may be used such that a scan line is not at the center 56.

The ARFIs or pushing pulses are transmitted at different times. The two push pulses are transmitted successively, separated in time by $\Delta t$. Any amount of time may separate the transmissions, such as 1 ms. The difference in time is selected so that the resulting shear waves will constructively interfere in the ROI. For example, the difference is less than 2 ms. Other maximum differences may be used depending on the size of the ROI. The difference in time is large enough to allow the first or initial ARFI to complete transmission before beginning the next ARFI, such as a time difference greater than 0.1 ms. In other embodiments, the transmissions of the ARFIs overlap and/or are simultaneous. Multiple beam transmission allows beams with different foci (i.e., different phase and/or delay profiles) to be generated based on summation of the electrical waveforms prior to application to the transducer.

The temporal difference is between beginnings for both ARFI transmissions or arrival of acoustic energy at the foci. The difference may be between endings, center, or other parts of the transmissions or acoustic energy arrival.

In response to the transmission of the pushing pulses to the different foci in sequence separated by the time difference, different shear waves are generated. For example, the shear waves are generated on opposite sides of the ROI in response to the ARFIs. The shear waves travel, in part, towards and/or in the ROI. The shear waves from the two push pulses will form an interference pattern within the ROI. If the ROI is homogeneous, the shear waves interfere constructively at lateral position $x=x_0+\Delta x$, where $x_0$ is the center of the ROI and/or the half-way point between the foci of the pushing pulses. The location of constructive interference is offset from the half-way point between the foci due to the time difference, $\Delta t$. At the location of constructive interference, the displacement magnitude is significantly higher compared to when a single push pulse is used.

In act 34, the ultrasound scanner scans the tissue of the patient. The scanning is repeated any number of times to determine the amount of tissue motion at different locations caused by the shear waves. Acts 36 and 38 provide one embodiment of scanning where a sequence is transmitted and resulting echoes are received. The detected tissue is compared to the reference scan of the tissue to determine displacement.

Doppler or B-mode scanning may be used for tracking the tissue responding to the stress. Ultrasound data is received in response to transmissions of ultrasound. The transmissions and receptions are performed for different laterally spaced locations, over an area, or over a volume. A sequence of transmissions and receptions are provided for each spatial location to track over time.

Acts 36 and 38 occur after the pushing pulses are applied and while the tissue is responding to the stress. For example, transmission and reception occur after application or change in the stress and before the tissue reaches a relaxed state. Ultrasound imaging is performed before, during and/or after the stress is applied.

In act 36 for tracking, the ultrasound scanner transmits a sequence of transmit beams or tracking pulses. A plurality of ultrasound signals is transmitted to the tissue responding to the stress. The plurality of signals is transmitted in separate transmit events. A transmit event is a contiguous interval where transmissions occur without reception of echoes responsive to the transmission. During the phase of transmitting, there is no receiving. Where a sequence of transmit events is performed, a corresponding sequence of receive events is also performed in act 38. A receive event is performed in response to each transmit event and before the next transmit event.

For a transmit event, a transmit beam is formed. Each transmit beam has a frequency response. For example, a transmit beam is formed by a 2.0 MHz pulse of 2 cycles. Any bandwidth may be provided. The pulses to form the transmit beams are of any number of cycles. Any envelope, type of pulse (e.g., unipolar, bipolar, or sinusoidal) or waveform may be used.

In act 38, the transducer receives ultrasound echoes in response to each transmit event. The transducer converts the echoes to receive signals, which are receive beamformed into ultrasound data representing one or more spatial locations. The response of tissue at scan lines for receive beams is detected.

Using reception of multiple receive beams in response to each tracking transmission, data for a plurality of laterally spaced locations may be received simultaneously. The entire ROI is scanned for each receive event by receiving along all the scan lines of the ROI in response to each transmit event. The monitoring is performed for any number of scan lines. For example, four, eight, sixteen, or thirty-two receive beams are formed in response to each transmission. FIG. 2 shows use of nine receive beams and corresponding scan lines. In other embodiments, other numbers of receive beams are formed in response to each transmission. In yet other embodiments, different transmit events and corresponding receive scan lines are scanned in sequence to cover the entire ROI.

The ultrasound scanner receives a sequence of receive signals. The reception is interleaved with the transmission of the sequence. For each transmit event, a receive event occurs. The receive event is a continuous interval for receiving echoes from the depth or depths of interest. After the transducer completes generation of acoustic energy for a given transmission, the transducer is used for reception of the responsive echoes. The transducer is then used to repeat another transmit and receive event pair for the same spatial location or locations, providing the interleaving (e.g., transmit, receive, transmit, receive, . . . ) to track the tissue response over time. The scanning of the ROI with ultrasound in act 34 is repetitive to acquire ultrasound data representing the tissue response at different times while the shear waves propagate through the ROI. Each repetition monitors the same region or locations for determining tissue response for those locations. Any number of M repetitions may be used, such as repeating about 50-100 times. The repetitions occur as frequently as possible while the tissue recovers from the stress, but without interfering with reception.

In act 40, the ultrasound scanner determines tissue motion. Tissue motion is detected as a displacement in one, two, or three dimensions. Motion responsive to the generated shear waves is detected from the received tracking or ultrasound data output from act 38. By repeating the transmitting of the ultrasound pulses and the receiving of the ultrasound echoes over the time, the displacements over the time are determined. The tissue motion is detected at different times. The different times correspond to the different tracking scans (i.e., transmit and receive event pairs).

Tissue motion is detected by estimating displacement relative to the reference tissue information. For example, the displacement of tissue along scan lines is determined. The displacement may be measured from tissue data, such as B-mode ultrasound data, but flow (e.g., velocity) or beamformer output information prior to detection (e.g., in-phase and quadrature (IQ) data) may be used.

As the tissue being imaged along the scan lines deforms, the B-mode intensity or other ultrasound data may vary. Correlation, cross-correlation, phase shift estimation, minimum sum of absolute differences or other similarity measure is used to determine the displacement between scans (e.g., between the reference and the current scan). For example, each IQ data pair is correlated to its corresponding reference to obtain the displacement. Data representing a plurality of spatial locations is correlated with the reference data. As another example, data from a plurality of spatial locations (e.g., along the scan lines) is correlated as a function of time. For each depth or spatial location, a correlation over a plurality of depths or spatial locations (e.g., kernel of 64 depths with the center depth being the point for which the profile is calculated) is performed. The spatial offset with the highest or sufficient correlation at a given time indicates the amount of displacement. For each location, the displacement as a function of time is determined. Two or three-dimensional displacement in space may be used. One-dimensional displacement along a direction different from the scan lines or beams may be used.

The detection of tissue motion occurs while or after the echoes are received. The received information is used for detection as the data is received. In one embodiment, the received information is stored and may be used for later detection.

For a given time or repetition of the scanning, the displacements at different locations are determined. The locations are distributed in one, two, or three dimensions. For example, displacements at different laterally spaced locations are determined from averages of displacements of different depths in the ROI. Different locations have the same or different displacement amplitude. These profiles of displacement as a function of location are determined for different times, such as for each repetition of the scanning. Line fitting or interpolation may be used to determine displacement at other locations and/or other times.

The displacements are responsive to the plurality of shear waves generated by the plurality of pushing pulses transmitted to different foci. Due to the origin locations of the shear waves and the relative timing of the scanning for displacement, any given location at any given time may be subject to no shear wave-caused displacement, displacement from one but not another of the shear waves, or displacement caused by both the shear waves. At some time, there is a location subjected to a maximum or constructive interference from both shear waves.

Figure 3:
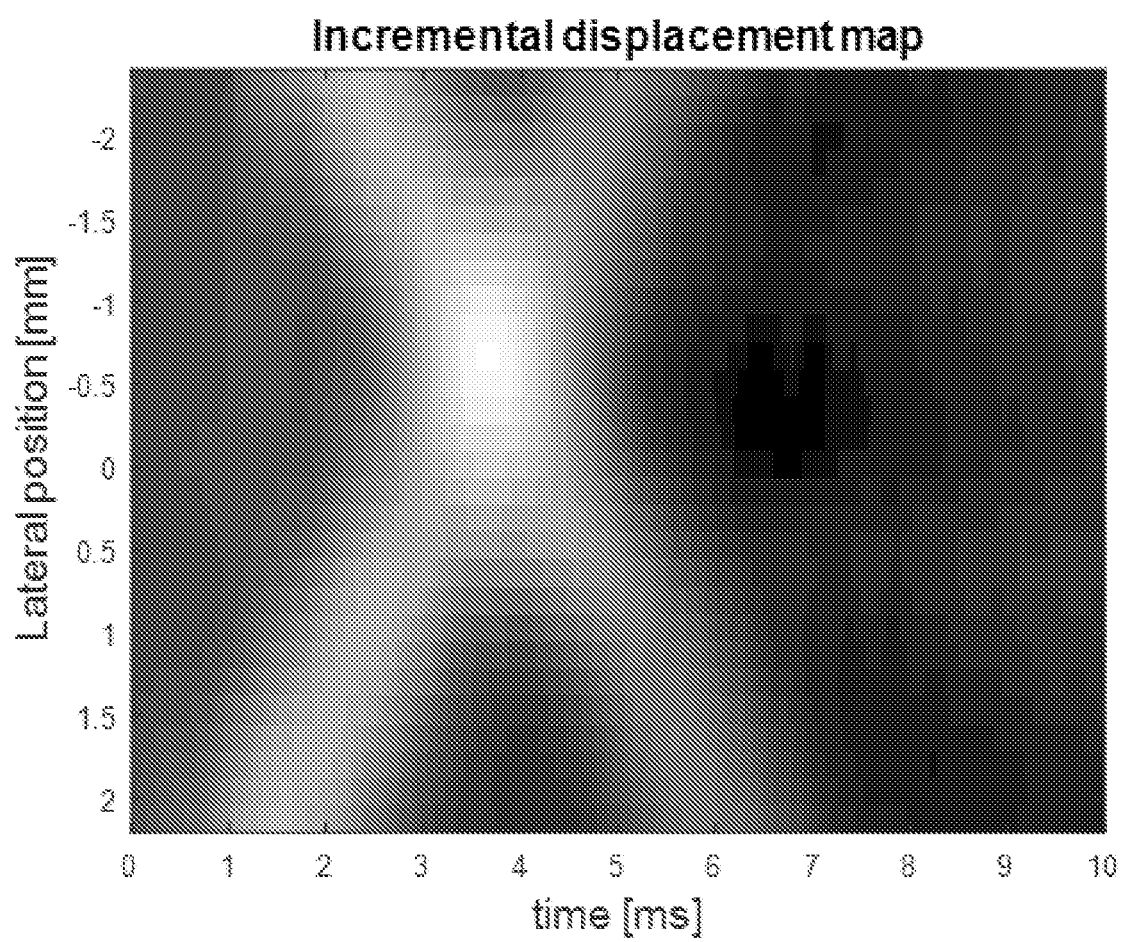
FIG. 3 shows an example displacement map for a region of tissue with constructive interference from multiple shear waves.

FIG. 3 shows an example displacement map. The displacement map is generated in a tissue mimicking phantom using two ARFI push pulses at opposite sides of the ROI, and separated in time by $\Delta t=1$ ms. The map represents displacements at different locations as a function of time. Displacements along the x-axis (time) shows displacement for each lateral position at a depth as a function of time. Displacements along the y-axis (lateral position) shows displacements for each time as a function of lateral position. Lighter grayscale represents greater displacement. The highest displacement magnitude is at the lateral location of constructive interference. In FIG. 3, this highest displacement magnitude occurs around lateral position 0.68 mm from the center of the ROI at time 3.8 ms. Other positions and times may result.

In act 42, the ultrasound scanner determines the position of coherence of the shear waves. In the example of FIG. 3, the image processor determines 0.68 mm as the lateral position with the maximum displacement. The peak displacement may be identified by finding a maximum displacement. The displacements are searched to find the maximum. The search may be constrained, such as by requiring an average of adjacent displacements to be within a given level of the peak. The peak displacement may be calculated from curves of displacements as a function of lateral position, from curves of displacements as a function of time (i.e., temporal profiles of displacements), or a collection of the displacements. The maximum displacement indicates the peak displacement.

The peak displacement represents the maximum constructive interference of the shear waves. The magnitude of this displacement is larger than the magnitude resulting from any fewer number of shear waves.

The position of constructive interference of the shear waves is determined. The peak occurs at a position. By finding the peak displacement, the position of the coherent sum of the shear waves is found. In the example of FIGS. 2 and 3, the lateral position is found.

Figure 4:
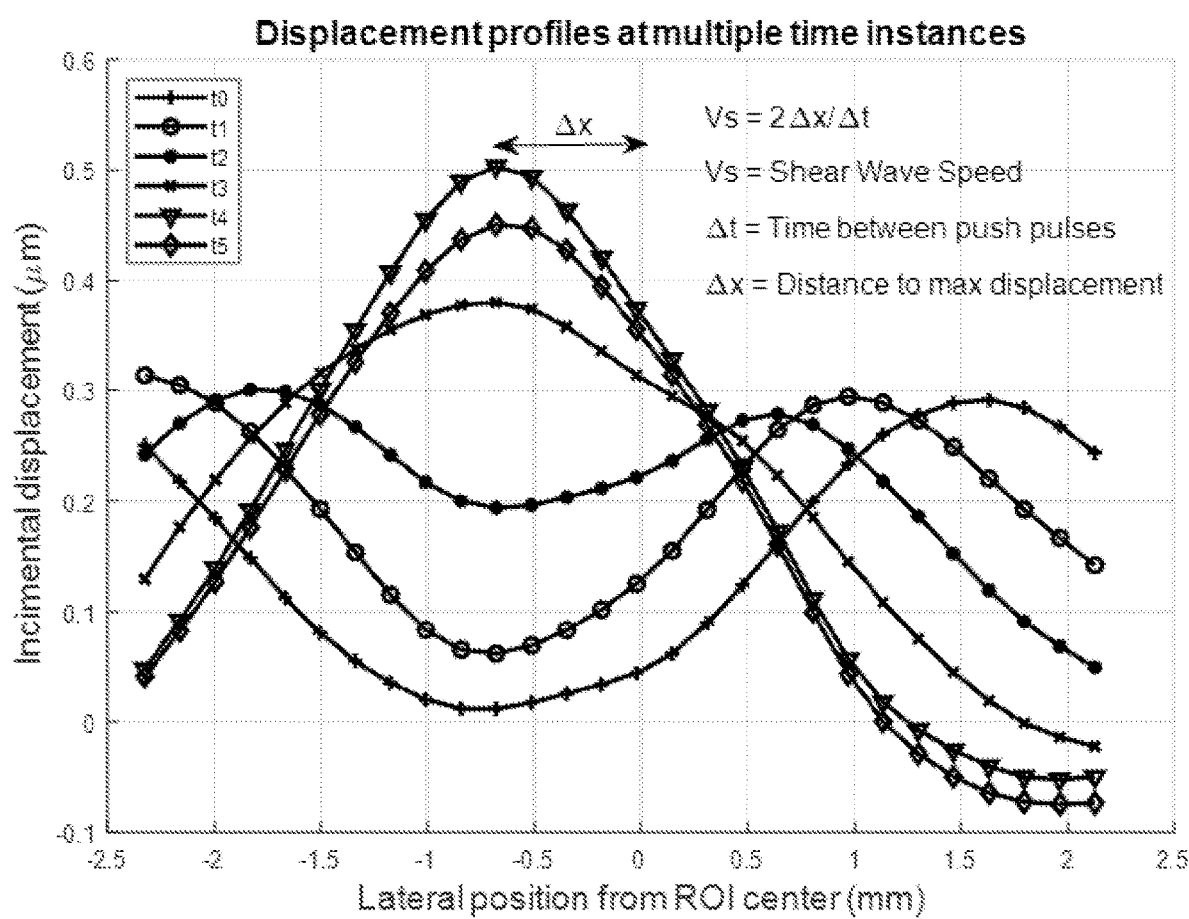
FIG. 4 shows example of lateral displacement profiles for different times in a region of interest.

FIG. 4 shows another representation of determining the position. The same data used for FIG. 3 is used in FIG. 4. In FIG. 4, lines are fit to the displacement as a function of lateral position. Each curve represents the lateral displacement profile at a different time (i.e., different repetition of the tracking scan). The location (e.g., lateral position) at which the maximum displacement in these lateral distributions is found. By using line fitting, the location of the maximum may be different than any location sampled in the scanning (i.e., sub-sampling resolution). In the example of FIG. 4, the maximum displacement occurs at the lateral position of 0.68 mm with a magnitude of 0.5 microns of displacement. The time of occurrence is not used, but may be used in other embodiments.

The change in position from the half-way point (e.g., from the center of the ROI for equal distant foci) is detected. Referring to FIG. 2, the lateral position is measured from a zero location that is half-way between the foci 60 of the push pulses 52, 54. With the center 56 of the ROI 62 being half way between the foci, the center 56 is lateral position 0.00. The lateral position 58 of the constructive interference is a distance from the center 56, so represents a difference in distance, $\Delta x$, from the center or half-way point. The absolute value of this difference is used to calculate the velocity. Where the half-way point is not designated as lateral position 0.00 (i.e., the origin), then the difference between the half-way point (e.g., center 56) and the position of the maximum (e.g., location 58) is calculated. The difference is a one, two, or three-dimensional distance. The magnitude of the difference is used.

In other embodiments, the location of coherence is found based on a shape of a profile of displacements. The profile of displacements is over time or space. A two-dimensional distribution of displacements along both time and space may be used. By template matching or other process, the shape is used to determine the location of coherence. At the location of coherence, the profiles in space and time intersecting or for that location will have a different shape than at other locations or times. The shape of the profile or a characteristic derived from the profile may be used to identify the location.

In act 44 of FIG. 1, the ultrasound scanner calculates a shear wave speed of the tissue. The shear wave speed of the tissue is a velocity of the shear waves passing through the tissue. Different tissues have different shear wave speed. A same tissue with different elasticity and/or stiffness has different shear wave speed. Other viscoelastic characteristics of tissue may result in different shear wave speed.

The shear wave speed is calculated based on the amount of time between the pushing pulses (i.e., $\Delta t$) and the location of the coherent interference. The shear wave speed is estimated by finding the lateral position corresponding to the peak of the displacement profile with highest amplitude. The position of constructive interference relative to the different foci and a time difference between the pushing pulses are used with or without other information to estimate velocity.

In one embodiment, the shear wave speed is calculated as two times a distance of the location of coherence from a center of the region of interest, divided by the time difference between ARFIs. This shear wave speed is represented by:

$$V_S = \frac{2\Delta x}{\Delta t},$$

where $V_s$ is the velocity of shear. The shear wave speed is a function of a difference of the position from a center between foci, divided by the time difference. Other functions may be used, such as to account for simultaneous transmission of the ARFIs.

In the example of FIGS. 3 and 4, $\Delta x$ is 0.68 and $\Delta t$ is 1 ms. For this homogenous phantom, the estimated shear wave speed is 1.36 m/s. This may be more accurate than shear wave imaging using a single shear wave. In the same phantom with less noise issues than a patient but using just one ARFI at a same amplitude, the shear wave speed is measured as 1.31 m/s, showing the results are at least comparable. The SNR should be higher with use of coherence of shear waves.

Other characteristics of the tissue may be estimated from the location and/or time of coherence. The magnitude of the peak displacement normalized for attenuation, time to reach the peak displacement, Young's modulus, or other elasticity values may be estimated. Any viscoelastic information may be estimated.

In act 46, the ultrasound scanner generates an output of the shear wave speed. The output is a graph, alphanumeric text, and/or an image of the shear wave speed of tissue of the patient.

To create a spatial image in act 46, the shear wave speeds at different locations are estimated. The transmitting of the pushing pulses, the scanning, the determining of displacements, determining the position of coherence, and the estimating are repeated for different spatial locations or ROIs. The pushing pulses may not be repeated where the same pushing pulses are used to measure at different depths. The resulting estimates of velocity for different locations are used to generate a shear wave speed image representing distribution of shear speed along one, two, or three dimensions. The output velocities for the different spatial locations are used in imaging, such as by color or grayscale modulating of different pixels or voxels by the velocity.

Alternatively or additionally, the image is of alphanumeric text (e.g., "1.36 m/s") as the image or overlaid as an annotation on a B-mode or flow-mode image of the tissue. A graph, table, or chart of velocity or velocities may be output as the image. Due to the use of coherence, the output velocity may be more reliably determined (e.g., requiring less repetition to obtain) and/or may be more accurate due to better SNR.

FIG. 5 shows one embodiment of a system 10 for shear speed imaging. Coherence of multiple shear waves originating at different locations is used to estimate shear velocity of tissue of a patient. The system 10 implements the method of FIG. 1 or other methods.

The system 10 is a medical diagnostic ultrasound imaging system or ultrasound scanner. In alternative embodiments, the system 10 is a personal computer, workstation, PACS station, or other arrangement at a same location or distributed over a network for real-time or post acquisition imaging, so may not include the beamformers 12, 16 and transducer 14.

The system 10 includes a transmit beamformer 12, a transducer 14, a receive beamformer 16, an image processor 18, a display 20, and a memory 22. Additional, different or fewer components may be provided. For example, a user input is provided for manual or assisted selection of display maps, selection of tissue properties to be determined, region of interest selection, selection of transmit sequences, or other control.

The transmit beamformer 12 is an ultrasound transmitter, memory, pulser, analog circuit, digital circuit, or combinations thereof. The transmit beamformer 12 is configurable to generate waveforms for a plurality of channels with different or relative amplitudes, delays, and/or phasing.

The transmit beamformer 12 is configured to transmit pulses. Upon transmission of acoustic waves from the transducer 14 in response to the generated waves, one or more beams are formed. ARFI transmissions are generated by the transmit beamformer 12. Two or more pushing pulses are transmitted at different times to different locations relative to tissue of interest of the patient. For tracking tissue displacement, a sequence of transmit beams covering the ROI are generated. The sequences of transmit beams are generated to scan a two or three-dimensional region. Sector, vector, linear, or other scan formats may be used. The transmit beamformer 12 may generate a plane wave or diverging wave for more rapid scanning.

The transmit beams are formed at different energy or amplitude levels. Amplifiers for each channel and/or aperture size control the amplitude of the transmitted beam. The ARFI transmit beams may have greater amplitudes than for imaging or detecting tissue motion. Alternatively or additionally, the number of cycles in the ARFI pulse or waveform used is typically greater than the pulse used for tracking (e.g., 100 or more cycles for ARFI and 1-6 cycles for tracking).

The transducer 14 is a 1-, 1.25-, 1.5-, 1.75-, or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer. The elements connect with channels of the transmit and receive beamformers 12, 16.

The transmit beamformer 12 and receive beamformer 16 connect with the same elements of the transducer 14 through a transmit/receive switch or multiplexer. The elements are shared for both transmit and receive events. One or more elements may not be shared, such as where the transmit and receive apertures are different (only overlap or use entirely different elements).

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to a transmission. In alternative embodiments, the receive beamformer 16 is a processor for generating samples using Fourier or other transforms. The receive beamformer 16 may include channels for parallel receive beamforming, such as forming two or more receive beams in response to each transmit event. The receive beamformer 16 outputs beam summed data, such as IQ or radio frequency values, for each beam.

The receive beamformer 16 operates during gaps in the sequence of transmit events for tracking. By interleaving receipt of signals with the tracking transmit pulses, a sequence of receive beams are formed in response to the sequence of transmit beams. After each transmit pulse and before the next transmit pulse, the receive beamformer 16 receives signals from acoustic echoes. Dead time during which receive and transmit operations do not occur may be interleaved to allow for reverberation reduction.

The receive beamformer 16 outputs beam summed data representing spatial locations at a given time. Data for different lateral locations (e.g., azimuth spaced sampling locations along different receive scan lines), locations along a line in depth, locations for an area, or locations for a volume are output. Dynamic focusing may be provided. The data may be for different purposes. For example, different scans are performed for B-mode or tissue data than for shear wave velocity estimation. Data received for B-mode or other imaging may be used for estimation of the shear wave velocity. The shear wave at locations spaced from the foci of the pushing pulses are monitored to determine velocity of the shear waves using coherent interference of the shear waves.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, network, server, group of processors, data path, combinations thereof, or other now known or later developed device for detecting and processing information for display from beamformed ultrasound samples. In one embodiment, the processor 18 includes one or more detectors and a separate processor. The processor 18 may be one or more devices. Multiprocessing, parallel processing, or processing by sequential devices may be used.

The processor 18 performs any combination of one or more of the acts 40-46 shown in FIG. 1. The processor 18 is configured by software, hardware, and/or firmware.

Prior to or after detection, the processor 18 is configured to detect displacements of tissue responding to acoustic radiation force. Using correlation, other measure of similarity, or other technique, the movement of tissue relative to a reference is determined from the ultrasound data. By spatially offsetting a tracking set of data relative to a reference set of data in one, two, or three-dimensional space, the offset with the greatest similarity indicates the displacement of the tissue. The processor 18 detects displacement for each time and location. Some of the detected displacements may have magnitudes responsive to a passing shear wave or shear waves.

The processor 18 is configured to determine a velocity of shear in the tissue. The determination is based on the signals from tracking the tissue responding to the shear waves created by multiple ARFIs. The signals are used to detect the displacements. To determine the velocity, the displacements are used.

A difference in (a) location of a greatest amplitude displacement due to shear waves responsive to the multiple pushing pulses from (b) a half-way point between the different locations is determined. The location of the greatest amplitude is a greatest of the displacements over time and location. For example, the displacements as a function of location at different times are examined to find the largest magnitude displacement. This greatest displacement represents the better signal-to-noise ratio resulting from constructive interference of the multiple shear waves.

A difference of the different times of transmission of the ARFIs is also looked-up, recorded, or determined. The time of transmission is based on the start, end, or other point in the ARFI transmission or start, end, or other point when the acoustic energy arrives at the focus.

The processor 18 is configured to determine the velocity of the shear wave in the tissue from the spatial difference and the temporal difference. In one embodiment, the velocity is two times the difference in location from the half-way point, divided by the difference of the different times. Other functions may be used.

The processor 18 generates display data, such as annotation, graphic overlay, and/or image. The display data is in any format, such as values before mapping, gray scale or color-mapped values, red-green-blue (RGB) values, scan format data, display or Cartesian coordinate format data, or other data. The processor 18 outputs velocity information appropriate for the display device 20, configuring the display device 20. Outputs to other devices may be used, such as outputting to the memory 22 for storage, output to another memory (e.g., patient medical record database), and/or transfer over a network to another device (e.g., a user computer or server).

The display device 20 is a CRT, LCD, projector, plasma, printer, or other display for displaying shear velocity, graphics, user interface, validation indication, two-dimensional images, or three-dimensional representations. The display device 20 displays ultrasound images, the velocity, and/or other information. For example, the display 20 outputs tissue response information, such as a one, two, or three-dimensional distribution of the velocity. Velocities for different spatial locations form an image. Other images may be output as well, such as overlaying the velocity as a color-coded modulation on a gray scale B-mode image.

In one embodiment, the display device 20 outputs an image of a region of the patient, such as a two-dimensional Doppler tissue or B-mode image. The image includes a location indicator for the velocity. The location indicator designates the imaged tissue for which a velocity value is calculated. The velocity is provided as an alphanumeric value on or adjacent the image of the region. The image may be of the alphanumeric value with or without spatial representation of the patient.

The processor 18 operates pursuant to instructions stored in the memory 22 or another memory. The memory 22 is a computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The memory 22 alternatively or additionally stores data used in estimation of velocity using coherent interference from two or more shear waves. For example, the transmit sequences and/or beamformer parameters for ARFI and tracking are stored. As another example, the ROI, received signals, detected displacements, determined location of maximum magnitude displacement, the difference of the location of maximum from the half-way point between ARFI foci, a time difference between transmission of different ARFIs or generating of different shear waves, fit lines, and/or estimated velocity or velocities are stored.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for shear speed imaging with an ultrasound scanner, the method comprising:

transmitting first and second acoustic radiation force pulses from a transducer of the ultrasound scanner to opposite sides of a region of interest of tissue of a patient and separated in time by a first amount, first and second shear waves being generated on the opposite sides due to the first and second acoustic radiation force pulses;

repetitively scanning, by the ultrasound scanner, the region of interest with ultrasound as the first and second shear waves propagate in the region of interest;

detecting a location of a greater displacement in the region of interest due to coherence of the first and second shear waves at the location, the location determined from data obtained by the scanning;

calculating a shear wave speed of the tissue as a function of the first amount of the time and the location; and generating an image of the shear wave speed of the tissue of the patient.

2. The method of claim 1 wherein transmitting comprises transmitting the first and second acoustic radiation force pulses an equal distance from a center of the region of interest on the opposite sides.

3. The method of claim 1 wherein transmitting comprises transmitting with the first and second acoustic radiation force pulses having a same center frequency.

4. The method of claim 1 wherein repetitively scanning comprises repetitively transmitting simultaneous tracking pulses over the region of interest and receiving acoustic responses responsive to the tracking pulses.

5. The method of claim 1 wherein detecting the location comprises detecting lateral distributions of displacements across the region of interest at different times and finding the location as a maximum displacement of the lateral distributions.

6. The method of claim 1 wherein detecting the location comprises detecting a change in position from a center of the region of interest.

7. The method of claim 1 wherein detecting comprise detecting the location as having a greatest coherence of the first and second shear waves.

8. A method for shear speed imaging with an ultrasound scanner, the method comprising:

transmitting first and second acoustic radiation force pulses from a transducer of the ultrasound scanner to opposite sides of a region of interest of tissue of a patient and separated in time by a first amount, first and second shear waves being generated on the opposite sides due to the first and second acoustic radiation force pulses;

repetitively scanning, by the ultrasound scanner, the region of interest with ultrasound as the first and second shear waves propagate in the region of interest;

detecting a location of a greater displacement in the region of interest due to coherence of the first and second shear waves at the location, the location determined from data obtained by the scanning;

calculating a shear wave speed of the tissue as a function of the first amount of the time and the location, wherein calculating the shear wave speed comprises calculating the shear wave speed as two times a distance of the location from a center of the region of interest, divided by the first amount; and generating an image of the shear wave speed of the tissue of the patient.

9. The method of claim 1 wherein generating the image comprises generating the image with alphanumeric text representation of the shear wave speed in the tissue.

10. The method of claim 1 further comprising repeating the transmitting, scanning, determining and calculating, and wherein generating the image comprises generating the image as a one, two, or three-dimensional distribution of the shear wave speeds in the tissue of the patient.

11. A method for shear speed imaging with an ultrasound scanner, the method comprising:

transmitting first and second acoustic radiation force pulses from a transducer of the ultrasound scanner to opposite sides of a region of interest of tissue of a patient and separated in time by a first amount, first and second shear waves being generated on the opposite sides due to the first and second acoustic radiation force pulses, wherein transmitting comprises transmitting with foci at a depth greater than 8 cm;

repetitively scanning, by the ultrasound scanner, the region of interest with ultrasound as the first and second shear waves propagate in the region of interest;

detecting a location of a greater displacement in the region of interest due to coherence of the first and second shear waves at the location, the location determined from data obtained by the scanning, wherein detecting the location comprises detecting the location at the depth greater than 8 cm;

calculating a shear wave speed of the tissue as a function of the first amount of the time and the location, and wherein calculating comprises calculating the shear wave speed at the depth greater than 8 cm; and generating an image of the shear wave speed of the tissue of the patient.

* * * * *